United States Patent
Ren et al.

(10) Patent No.: US 11,045,794 B2
(45) Date of Patent: Jun. 29, 2021

(54) SUPPORTED CATALYST USED FOR SYNTHESIZING POLYETHER AMINE, AND MANUFACTURING METHOD

(71) Applicant: Wanhua Chemical Group Co., Ltd., Shandong (CN)

(72) Inventors: Shujie Ren, Shandong (CN); Congying Zhang, Shandong (CN); Xin Li, Shandong (CN); Zhenguo Liu, Shandong (CN); Xiaolong Wang, Shandong (CN); Lei Tang, Shandong (CN); Zhipeng Liu, Shandong (CN); Zhanyu Gao, Shandong (CN); Jian Wu, Shandong (CN); Cong Wang, Shandong (CN); Yuan Li, Shandong (CN); Qingmei Jiang, Shandong (CN); Jinhong Song, Shandong (CN); Weiqi Hua, Shandong (CN); Hao Ding, Shandong (CN)

(73) Assignee: Wanhua Chemical Group Co., Ltd.

( * ) Notice: Subject to any disclaimer, the term of this patent is extended or adjusted under 35 U.S.C. 154(b) by 30 days.

(21) Appl. No.: 16/323,671

(22) PCT Filed: Aug. 24, 2016

(86) PCT No.: PCT/CN2016/096531
§ 371 (c)(1),
(2) Date: Feb. 6, 2019

(87) PCT Pub. No.: WO2018/032522
PCT Pub. Date: Feb. 22, 2018

(65) Prior Publication Data
US 2019/0201878 A1     Jul. 4, 2019

(30) Foreign Application Priority Data

Aug. 18, 2016  (CN) .......................... 201610700895.9

(51) Int. Cl.
| | | |
|---|---|---|
| *B01J 21/04* | (2006.01) | |
| *B01J 21/06* | (2006.01) | |
| *B01J 21/08* | (2006.01) | |
| *B01J 21/10* | (2006.01) | |
| *B01J 21/12* | (2006.01) | |
| *B01J 21/14* | (2006.01) | |
| *B01J 23/44* | (2006.01) | |
| *B01J 23/56* | (2006.01) | |
| *B01J 23/89* | (2006.01) | |
| *B01J 37/02* | (2006.01) | |
| *B01J 37/03* | (2006.01) | |
| *B01J 37/08* | (2006.01) | |

(Continued)

(52) U.S. Cl.
CPC ........... *B01J 23/8993* (2013.01); *B01J 21/04* (2013.01); *B01J 23/44* (2013.01); *B01J 23/46* (2013.01); *B01J 23/56* (2013.01); *B01J 23/8926* (2013.01); *B01J 23/8946* (2013.01); *B01J 23/8966* (2013.01); *B01J 37/0213* (2013.01); *B01J 37/0236* (2013.01); *B01J 37/035* (2013.01); *B01J 37/08* (2013.01); *B01J 37/18* (2013.01); *C07C 213/02* (2013.01); *C08G 65/325* (2013.01); *C08G 65/3255* (2013.01); *C08G 65/33306* (2013.01)

(58) Field of Classification Search
CPC . B01J 21/04; B01J 21/06; B01J 21/063; B01J 21/066; B01J 21/08; B01J 21/10; B01J 21/12; B01J 21/14; B01J 23/44; B01J 23/464; B01J 23/56; B01J 23/892; B01J 23/8926; B01J 23/8946; B01J 23/8953; B01J 23/8966; B01J 23/8973; B01J 23/8993; B01J 37/0213; B01J 37/0236; B01J 37/035; B01J 37/08; B01J 37/18; C07C 213/02; C08G 65/325; C08G 65/3255; C08G 65/33306

See application file for complete search history.

(56) References Cited

U.S. PATENT DOCUMENTS

| | | |
|---|---|---|
| 3,654,370 A | 4/1972 | Yeakey |
| 4,014,933 A | 3/1977 | Boettger et al. |

(Continued)

FOREIGN PATENT DOCUMENTS

| | | |
|---|---|---|
| CN | 1546550 A | 11/2004 |
| CN | 101842345 A | 9/2010 |

(Continued)

OTHER PUBLICATIONS

International Search Report PCT/CN2016/096531 dated Apr. 12, 2017.

(Continued)

*Primary Examiner* — Cam N. Nguyen
(74) *Attorney, Agent, or Firm* — Lerner, David, Littenberg, Krumholz & Mentlik, LLP

(57) ABSTRACT

A supported catalyst used for synthesizing a polyether amine, and a manufacturing method of the catalyst. The catalyst comprises: a porous oxide as a support; Ni, Cu, Pd, and Rh as active components; and one or more of any of Zr, Cr, Mo, Fe, Zn, Sn, Bi, Ce, La, Hf, Sr, Sb, Mg, Be, Re, Ta, Ti, Sc, Ge and related metals as an auxiliary agent. The catalyst can be used in an amination reaction for a large molecular weight polyether polyol, and is particularly active and selective for an amination reaction of a low molecular weight polyether polyol. The catalyst has a simple and economic manufacturing technique and good potential for future applications.

20 Claims, No Drawings

(51) Int. Cl.
*B01J 37/18* (2006.01)
*C07C 213/02* (2006.01)
*C08G 65/325* (2006.01)
*C08G 65/333* (2006.01)
*B01J 23/46* (2006.01)

(56) References Cited

U.S. PATENT DOCUMENTS

| | | | |
|---|---|---|---|
| 4,152,353 A | 5/1979 | Habermann | |
| 4,153,581 A | 5/1979 | Habermann | |
| 4,209,424 A | 6/1980 | Le Goff et al. | |
| 4,766,245 A | 8/1988 | Larkin et al. | |
| 4,973,761 A | 11/1990 | Schoenleben et al. | |
| 5,003,107 A | 3/1991 | Zimmerman et al. | |
| 5,352,835 A | 10/1994 | Dai et al. | |
| 6,046,359 A | 4/2000 | Wulff-Doring et al. | |
| 6,576,588 B2* | 6/2003 | Ryu | C07C 7/167 502/331 |
| 7,067,455 B2* | 6/2006 | Chen | B01J 23/72 502/305 |
| 7,268,097 B2* | 9/2007 | Katsuno | B01J 20/0222 208/217 |
| 7,605,108 B2* | 10/2009 | Wakamatsu | B01J 37/16 502/302 |
| 7,915,196 B2* | 3/2011 | Parent | B01J 23/83 502/335 |
| 7,976,804 B2* | 7/2011 | Jantsch | B01D 53/8628 423/239.1 |
| 8,664,454 B2* | 3/2014 | Weiner | B01J 23/80 568/885 |
| 8,975,200 B2* | 3/2015 | Zhou | B01J 21/08 501/100 |
| 9,308,523 B2* | 4/2016 | Zhou | B01J 23/626 |
| 9,381,500 B2* | 7/2016 | Zhou | B01J 37/0244 |
| 9,486,781 B2* | 11/2016 | Zhou | B01J 37/0207 |
| 9,597,663 B2* | 3/2017 | Inoda | B01J 23/58 |
| 10,065,910 B2* | 9/2018 | Shen | B01J 23/75 |
| 2010/0069671 A1 | 3/2010 | Buehring et al. | |
| 2010/0240894 A1 | 9/2010 | Ernst et al. | |

FOREIGN PATENT DOCUMENTS

| | | |
|---|---|---|
| CN | 102336903 A | 2/2012 |
| CN | 102875795 A | 1/2013 |
| CN | 103709391 A | 4/2014 |
| CN | 104383918 A | 3/2015 |
| CN | 105008431 A | 10/2015 |
| CN | 105399940 A | 3/2016 |
| GB | 12008.3 A | 10/1918 |
| WO | 2015069531 A1 | 5/2015 |

OTHER PUBLICATIONS

Database WPI Week 201640 Thomson Scientific, London, GB; AN 2016-184704 -& CN 105 399 940 A (Wanhua Chem Group Co LTO) Mar. 16, 2016 (Mar. 16, 2016).

Extended European Search Report for Application No. 16913278.4 dated Feb. 28, 2020, 9 pages.

* cited by examiner

US 11,045,794 B2

SUPPORTED CATALYST USED FOR SYNTHESIZING POLYETHER AMINE, AND MANUFACTURING METHOD

CROSS REFERENCE TO RELATED APPLICATIONS

The present application is a national phase entry under 35 U.S.C. § 371 of International Application No. PCT/CN2016/096531, filed Aug. 24, 2016, which claims priority from Chinese Patent Application No. 201610700895.9 filed Aug. 18, 2016, all of which are hereby incorporated herein by reference.

TECHNICAL FIELD

The present invention relates to a supported catalyst used for synthesizing a polyether amine, a preparation method thereof and a method for preparing a polyether amine by amination of a polyether polyol, and belongs to the field of polymer synthesis.

BACKGROUND OF ART

Polyether amine, also known as Amino-Terminated Polyether (ATPE), is a type of polyoxyalkylene compound in which the molecular main chain is a polyether skeleton and the terminals are terminated by amino. Most of these ATPEs are obtained by using polyether (polyethylene glycol, polyoxypropylene ether, etc.) as the reaction raw material and converting the terminal hydroxyls of polyether polyol into corresponding amine groups or amino groups (the terminal group is usually a primary amine, a secondary amine or a polyamine containing active hydrogen) by employing different chemical treatment methods. At present, only Huntsman and BASF have industrialized amino-terminated polyether amines around the world.

Due to the reactivity of amine groups or amino groups at the terminal ends of the polyether skeleton, polyether amine can interact with a variety of reactive groups, such as epoxy groups and isocyanate groups; in addition, due to the presence of ether linkages in the polyether chain, polyether amine can also dissolve easily in a variety of organic substances, which greatly expands the application range of polyether amines in the industrial field. Therefore, polyether amines are widely used in the fields of epoxy resin curing agents, polyurethane (polyurea) industries, and gasoline detergent dispersants because of their superior properties.

The methods for synthesizing polyether amines mainly include reductive amination method, leaving group method and polyether nitrile reduction method. Wherein, the reductive amination method is also called as hydroamination method, and since its process route is the most advanced, the quality of the products is the most stable and it is also more environmentally friendly, the reductive amination method has become the main method for industrial production of polyether amines at home and abroad.

The key to this production process is the choice and preparation of the catalyst. Catalysts suitable for reductive amination contain metals such as Ni, Co and Cu as active components, which sometimes are referred to as hydrogenation/dehydrogenation catalysts, because they are active in these two types of reactions. Other elements in the periodic table are also often introduced into the catalyst to give it the best activity or selectivity.

U.S. Pat. No. 3,654,370 discloses a process for the catalytic amination of a polyether diol having a molecular weight of 1000 and a polyether triol having a molecular weight of 1500 using a continuous tubular reactor, and the catalyst thereof is prepared by a coprecipitation method and contains 75% of Ni, 23% of Cu and 2% of Cr. The catalyst has the problems of complicated preparation process, poor strength and fragility.

U.S. Pat. No. 4,766,245 discloses a Raney nickel catalyst for the amination of polyether polyols. The catalyst comprises 60-75% of Ni and 40-25% of Al, but the catalyst is only suitable for the amination reaction of polyether polyols having molecular weight of more than 500.

U.S. Pat. No. 4,014,933 discloses an alumina or silica supported Co—Ni—Cu catalyst and a process for the amination of polypropylene glycol. The catalyst comprises 10% of Co, 10% of Ni, 4% of Cu, and 0.4% of phosphoric acid, and the rest is $Al_2O_3$. The catalyst is suitable for the amination reaction of polyether polyols having molecular weight of more than 1400.

U.S. Pat. Nos. 4,152,353 and 4,153,581 disclose a catalyst of alumina supported Ni, Cu and auxiliary agent selected from one or two metals of Fe and Zn. The catalyst comprises 30% of Ni (or 30% of Co), 63% of Cu and 7% of Fe and/or Zn, and the rest is $Al_2O_3$. The catalyst has the problems of low activity and poor selectivity.

U.S. Pat. No. 4,209,424 discloses an alumina supported transition metal amination catalyst, and uses it for the amination of a polyether polyol. The catalyst comprises at least one or two of Ni, Co and Cu, wherein the metal content is 30-70%, the rest is $Al_2O_3$.

U.S. Pat. No. 4,973,761 discloses an amination catalyst of alumina supported Ni, Co and Cu, and uses it for the amination of polytetrahydrofuran ether glycol. The catalyst is suitable for amination of polyether polyols having molecular weight of 640 to 4000, but has problems of low catalyst activity and poor product selectivity.

U.S. Pat. No. 5,003,107 discloses an amination catalyst of alumina supported Ni, Co, Cr, and Mo, and uses it for the amination of polyoxytetramethylene glycol. The catalyst comprises 70-75% of Ni, 20-25% of Cu, 0.5-5% of Cr and 1-5% of Mo, and the rest is $Al_2O_3$. In the amination process of polytetrahydrofuran polyether with molecular weight of 1000-2000 using a continuous tubular reactor, the conversion rate of raw materials is 91-96%, and the product selectivity is 92-97%. The catalyst does not involve the amination of polyether polyols having a molecular weight of less than 500.

US20100069671 employs metals of at least 80 wt % of Co and Al, less than 5 wt % of Cu as a catalyst to catalyze the corresponding polyether polyol to prepare polyether amine, the catalyst is suitable for polyether polyols having molecular weight of more than 2000, and cannot be used for the amination of polyether polyols having molecular weight of less than 500.

CN1546550A discloses a process for the preparation of polyether amine by hydroamination of a polyfunctional amine having a molecular weight of 2000 and a trifunctional polyether having a molecular weight of 5000. Of which a skeleton nickel catalyst with 60-80 wt % of Ni, 10-35 wt % of Al, and 2-10 wt % of Cr is used. The catalyst is not suitable for the polyether amine preparation process by amination of polyether polyols containing various monomer skeletons such as ethylene oxide (EO) and/or propylene oxide (PO) and polyether polyols having average molecular weight of less than 500.

CN102336903A discloses an amination process of polyether polyols having molecular weight of more than 100, of which a skeleton nickel catalyst having a Ni content of 85-95 wt % and an Al content of 5-15 wt % is used. The catalyst has a higher activity for the amination of the polyether polyols having molecular weight of more than 1000, and for the amination of the polyether polyols having molecular weight of less than 500, the conversion of the raw material is 80-90%, and the selectivity of the product is 90-95%.

The above-mentioned catalysts of prior art encounter the problems of complicated preparation processes, fragility, high metal content and poor economy. At the same time, the catalysts of prior art are only suitable for the amination of polyether polyols with large molecular weight, while exhibiting poor activity and selectivity for the amination reaction of low molecular weight polyether polyols, especially polyether polyols having average molecular weight of less than 500.

SUMMARY OF THE INVENTION

The object of the present invention is to provide a supported catalyst for synthesizing a polyether amine, a preparation method thereof, and a method for preparing a polyether amine by amination of a polyether polyol. The catalyst can be used for catalyzing the amination reaction of a polyether polyol and has extremely high activity and selectivity.

In order to achieve one aspect of the above object, the technical solution adopted by the present invention of the supported catalyst for synthesizing a polyether amine is as follows:

A supported catalyst for synthesizing a polyether amine, wherein the catalyst comprises a support and active components, the active components comprise Ni, Cu, Pd and Rh, and each has a content as follows based on the total weight of the catalyst:

the content of Ni element is 1-15 wt %, preferably 4-12 wt %, more preferably 5-10 wt %;

the content of Cu element is 0.5-10 wt %, preferably 1-8 wt %, more preferably 3-5 wt %;

the content of Pd element is 0.1-1.0 wt %, preferably 0.5-0.8 wt %, more preferably 0.6-0.7 wt %;

the content of Rh element is 0.05-0.5 wt %, preferably 0.15-0.4 wt %, more preferably 0.2-0.3 wt %.

The catalyst of the present invention optionally further comprises an auxiliary agent which is selected from the group consisting of Zr, Cr, Mo, Fe, Zn, Sn, Bi, Ce, La, Hf, Sr, Sb, Mg, Be, Re, Ta, Ti, Sc, Ge and any combination thereof, preferably the group consisting of Zr, Ce, Mg, Mo, Ti, and any combination thereof, and more preferably Zr and/or Mg.

In a preferred embodiment of the present invention, the catalyst consists of a support, active components and an optional auxiliary agent. In the present invention, it should be noted that "optional" means things may or may not exist.

The content of the auxiliary agent is preferably 0-0.5 wt %, further preferably 0.05-0.45 wt %, more preferably 0.1-0.3 wt % based on the total weight of the catalyst to further enhance the catalytic effect thereof. In the present invention, when the content of a certain component is 0%, it means that this component is not contained.

The total content of the active components is preferably not less than 5 wt %, further preferably not less than 10 wt %, more preferably not less than 12 wt %, such as 11 wt %, 14 wt %, 16 wt %, 18 wt % or 20 wt %, based on the total weight of the catalyst, to further enhance the catalytic effect thereof. Of course, those skilled in the art will understand that excessively high content of active components will further increase the catalyst cost. In a preferred embodiment, the active components consist of Ni, Cu, Pd and Rh.

In the present invention, the support may be a porous oxide such as one or more of the group consisting of $\gamma$-$Al_2O_3$, $SiO_2$, MgO, $TiO_2$ and $ZrO_2$, preferably $\gamma$-$Al_2O_3$. The preparation method of the above porous oxides is well known in the art. For example, as to $\gamma$-$Al_2O_3$, $Al_2(SO_4)_3$ is formulated into a 6 wt % aqueous solution, and 20 wt % of $NH_3.H_2O$ is added, the reaction is kept for 1 h under strong stirring to obtain $Al(OH)_3$ precipitate. And then the aluminum hydroxide product is obtained by filtration, water washing and drying, which is molded by band extrusion and activated by calcination at 550° C. for 4 h to obtain the $\gamma$-$Al_2O_3$. Preferably the $\gamma$-$Al_2O_3$ has the following properties: specific surface area: 180-220 $m^2/g$, pore volume: 0.9-1.2 ml/g, pore diameter: 9-12 nm, mechanical strength: >50 N/cm, bulk density: 0.60-0.80 g/ml.

The support of the present invention may be in a variety of shapes, and the specific shape of the support may be designed and selected according to the reactors for catalyzing different polyether polyols and amination reagents (for example, it may be a kettle-type reactor, a fixed bed reactor, a fluidized bed reactor, a tubular-type reactor or a bubble tower reactor according to actual needs), including but not limited to one or more of sheet, strip and clover type.

The catalyst according to the present invention is suitable for the amination reaction of polyether polyols having weight average molecular weight of 90-7,000, preferably 100-5,000, more preferably 200-600, for example 300, 400 or 500.

In the art of the present invention, primary amines are usually prepared by reacting polyether polyols with ammonia under reductive amination process conditions. The reaction mechanism is generally considered to include that: in the presence of a catalyst, a hydroxyl is dehydrogenated to form a carbonyl, the carbonyl is aminated and dehydrated to form an olefinimine, and the olefinimine is reduced and converted to a terminal amino by hydrogenation catalysts. Research has found that a good selectivity to primary amines is generally achieved when ammonia is in excess and a secondary alcohol is used in the reaction under appropriate catalytic reaction conditions. However, under the same catalytic reaction conditions, when a primary alcohol is used as reactant, not only the selectivity of the primary amine in the reaction product is low, but also a significantly higher secondary amine product and significantly higher undesired "hydrogenolysis" by-products are favored. In particular, the hydrogenolysis by-products are formed by reductive decomposition or by formal addition of hydrogen to C—C, C—O and C—N bonds when the alcohol conversion rate is high.

In accordance with the present invention, we have surprisingly found that the synergistic effect generated by the specific combination of the active components of nickel, copper, palladium and rhodium in the catalyst can greatly reduce by-products (eg, monoamino and/or biamino by-products, dimethylmorpholine by-products generated by low molecular weight polyethers, etc.) in the amination process of polyether polyols, especially under the condition that the polyether polyol is completely converted, and thereby the selectivity and product yield of the primary amine are greatly improved. At the same time, due to the decrease of by-products, the viscosity of the product is lower, the color is lighter (i.e., the color number is smaller), and the additional value is higher.

In order to achieve another aspect of the above object, the method for preparing the supported catalyst provided by the present invention adopts the following technical solution:

A preparation method for a supported catalyst for synthesizing polyetheramines, comprising the following steps:

1) Preparation of a metal salt solution: weighing metal salts proportionally, and adding deionized water, alcohol or ketone solvents to prepare a metal salt solution; wherein the metal salts are the metal salts of the active components and the optional auxiliary agent;

2) Adsorption: using the support to adsorb the metal salt solution obtained in step 1) to obtain an adsorbed wet support;

3) Drying, calcining and reducing the wet support to obtain the supported catalyst.

In the step 1), the metal salts in the metal salt solution include but is not limited to one or more of metal halide, metal nitrate, organic acid metal salt, and the like, preferably one or more of metal nitrate, metal formate, metal acetate and metal oxalate, more preferably metal nitrate.

The ratio of the amount of each metal element in the metal salts can be determined according to the ratio of each active component and each component of the auxiliary agent in the foregoing catalyst, wherein the metal salt solution is an aqueous solution in which the metal salts are dissolved in water to form the metal salt solution, and the concentration thereof may be 5-60 wt %, such as 20 wt %, 30 wt % or 40 wt %.

In the step 2), the method for adsorbing the metal salt solution with the support is well known in the art, for example, the support may be impregnated with the metal salt solution obtained in the step 1), or the metal salt solution obtained in the step 1) may be sprayed on the support, thereby a adsorbed wet support is obtained. Those skilled in the art understand that the solution concentration, the impregnating time or the spray amount can be adjusted to adjust the adsorption amount of the metal salt in the support, thereby controlling the content of the active components or the auxiliary agent in the catalyst, and the adsorption process can be conducted for one time or repeatedly. In one embodiment, the volume ratio of the metal salt solution to the support can also be controlled within a suitable range, so that the metal salt solution can be substantially completely absorbed by the support or the solid-liquid mixture of the obtained support and the solution can be evaporated to remove excess solvent.

The impregnation process can be carried out in various ways, for example, impregnating the support with a solution comprising various metal salts, or mixing various metal salt solutions uniformly and impregnating it onto the support, or impregnating the support sequentially with different metal salt solutions; those skilled in the art understand that the impregnation process and the spraying process can be done in one step or in multiple steps.

In the step 3), a catalyst precursor is obtained firstly by giving drying and calcination treatment to the obtained support. The above treating processes are common in the art, wherein the drying condition may be: the drying temperature is 50° C.-120° C., preferably 60° C.-90° C.; the drying time is 4 h-24 h, preferably 8-12 h; and the calcination condition may be: the calcination temperature is 200° C.-600° C., preferably 300° C.-500° C.; the calcination time is 2 h-12 h, preferably 4 h-8 h.

The catalyst precursor obtained by drying and calcination treatments in the step 3) is subjected to reduction treatment after cooling to obtain the supported catalyst of the present invention, which can be used for the amination reaction of a polyether polyol, and the above reduction treating process is a common process in the art, for example, the catalyst precursor is subjected to reduction at a temperature of 100° C.-400° C., preferably 200° C.-300° C.; the reduction process is carried out in the presence of a gas containing hydrogen, wherein the reduction time is 1 h-24 h, preferably 4 h-16 h. The reduction process uses a gas containing hydrogen, such as pure hydrogen or a mixture of inert gas and hydrogen, the inert gas including but not limited to nitrogen, helium, neon, argon or krypton, preferably nitrogen; preferably, the volume content of the inert gas is 5%-95%, more preferably 50%-95% based on the total volume of the inert gas and hydrogen.

According to the preparation method of the present invention, in a preferred embodiment, the preparation method further comprises step 1a) preparation of a metal salt complex solution: forming a metal salt complex solution by reacting the metal salt solution with a ligand, and then performing step 2); That is, the metal salt solution obtained in the step 1) is further prepared into a metal salt complex solution instead of the metal salt solution itself to perform the treatment of step 2).

In step 1a), the ligand comprises an inorganic ligand and/or an organic ligand, and preferably is one or more of ammonia and organic amines, more preferably is one or more of ammonia, ethylenediaminetetraacetic acid (EDTA) and diethylamine, and further preferably is ammonia. The molar ratio of the metal element to the ligand in the metal salt complex solution is preferably 1:1-1:10, such as 1:3, 1:5 or 1:7.

According to the preparation method of the present invention, in a preferred embodiment, the preparation method further comprises step 2a) in-situ precipitation of $CO_2$: precipitating the metal salt complex on the adsorbed wet support obtained in step 2) by using carbon dioxide gas. That is, the adsorbed wet support obtained in step 2) is subjected to the treatment in the step 3) after the treatment in step 2a).

In step 2a), precipitating the metal salt complex (such as carbonate precipitation) on the adsorbed wet support by using carbon dioxide gas, and its reaction principle is well known in the art. The specific reaction can be carried out in a tubular reactor, wherein the gas containing carbon dioxide is introduced from one end of the reactor and vented from the other end, so that the gas can react with the metal salt complex on the support. The inlet speed of the gas can be determined by a person skilled in the art according to actual conditions, which will not be explored herein. In the present invention, the reaction condition for in-situ precipitation of $CO_2$ may be: performing the precipitation reaction in an atmosphere containing carbon dioxide at a reaction temperature of 20-50° C., preferably 30-40° C. for 2-10 h, preferably 4-6 h. In order to keep the precipitation reaction performing smoothly, the volume of carbon dioxide in the gas should be enough to sufficiently precipitate the adsorbed wet support in a controllable time, for example, the volume content of carbon dioxide in the gas is not less than 20 vol %, such as 50 vol % or 80 vol %. In addition, in order to accelerate the precipitation reaction, the reaction can also be carried out under a pressurized condition.

In order to achieve a further aspect of the above object, the method for preparing a polyether amine by amination of a polyether polyol provided by the present invention adopts the following technical solutions:

A method for preparing a polyether amine by amination of a polyether polyol, which is: subjecting the polyether polyol to a reductive amination reaction in the presence of hydrogen, an amination reagent and the supported catalyst of the present invention to prepare the polyether amine.

The catalyst of the present invention is particularly suitable for the reductive amination reaction of a polyol with polyether as skeleton unit; said polyether polyol preferably contains an ethylene oxide (EO) and/or propylene oxide (PO) skeleton, and has a weight average molecular weight of 90-7,000, preferably 100-5,000, more preferably 200-600, for example 300, 400 or 500; said polyether polyol contains more than two hydroxyls.

Those skilled in the art understand that the expression "contain an ethylene oxide (EO) and/or propylene oxide (PO) skeleton" means that the polyether polyol is prepared by using one or more of ethylene glycol, propylene glycol, trimethylolpropane (TMP) and neopentyl glycol (NPG) as initiator to react with PO and/or EO, and its specific preparation method is well known in the art and can make a specific reference to Chinese invention patents CN201210393578.9 and CN201310627712.1.

In the method for preparing a polyether amine according to the present invention, the animation reagent is an organic amine having C atoms no more than 10 and/or ammonia, and has the formula of $NHR_1R_2$, wherein $R_1$ and $R_2$ may be the same or different and are independently selected from the group consisting of hydrogen, methyl, ethyl, propyl and isopropyl, preferably the amination reagent is one or more of ammonia, methylamine and dimethylamine.

The process for preparing polyether amines of the present invention may be carried out intermittently or continuously, preferably continuously. The preparation of the polyether amines by a continuous process can be carried out in a tubular reactor in the form of liquid phase reaction or gas phase reaction.

In the present invention, preferably, the molar ratio of the animation reagent to the polyether polyol is (1-60):1, preferably (6-20):1, such as 10:1, 14:1 or 16:1. The molar ratio of hydrogen to polyether polyol is (0.01-1):1, preferably (0.05-0.5):1, such as 0.08:1, 0.1:1, 0.3:1 or 0.4:1.

Preferably, the space velocity of the polyether polyol is 0.01-3 $h^{-1}$, preferably 0.1-1.0 $h^{-1}$.

The reaction temperature of the reductive amination reaction of the present invention may be 100-300° C., preferably 150-250° C., particularly preferably 180-230° C.; and the reaction pressure (absolute pressure) may be 1-30 MPa, preferably 5-20 MPa, particularly preferably 10-18 MPa.

The reductive amination reaction of the present invention may or may not use a solvent, and the solvent may be selected from one or more of alcohols, ethers, and hydrocarbon compounds. Preferably the solvent includes but not limited to one or more of water, methanol, ethanol, benzene, cyclohexane, toluene, diethyl ether, THF, and MTBE (methyl tert-butyl ether). The reductive amination reaction of the present invention is preferably carried out without using a solvent.

The catalyst prepared according to the present invention can make the conversion rate of the raw material reach to about 100%, such as more than 99.9%, the selectivity of the polyether amine product reach to more than 99.0%, the product yield reach to more than 99.5%, and the content by-products reach to less than 0.5 wt %.

The beneficial effects of the present invention are:

(1) The active components Ni, Cu, Pd and Rh are introduced into the polyether catalyst, and the synergistic effect produced by the specific combination of Ni, Cu, Pd and Rh greatly reduces the content of by-products (including mono-amino and/or diamino by-products, dimethylmorpholine by-products generated by low molecular weight polyethers, etc.) in the amination process, especially under the condition that the polyether is converted completely, thereby greatly improving the selectivity and yield of polyether amine products.

(2) The catalyst of the present invention is not only suitable for the amination reaction of polyether polyols with large molecular weight, but also particularly suitable for the amination reaction of polyether polyols with low molecular weight (less than 500). The catalyst exhibits extremely high activity and selectivity in the amination reaction of polyether polyols with molecular weight of less than 500.

(3) The sintering resistance and stability of the catalyst of the present invention can be significantly improved by adding auxiliary agent elements.

(4) In the preparation process of the catalyst, it is preferred to use a metal salt complex solution such as a metal ammonium salt solution to impregnate the support, and compared with using a conventional metal salt aqueous solution (such as nitrate) or a metal molten salt solution to impregnate the support, the metal salt complex solution has a characteristic of low viscosity which is favorable for the sufficient absorption of the support, thereby improving the activity of the catalyst; at the same time, the metal salt complex solution has the advantages of: low corrosivity, easy to storage and transport, and economical to treat;

In addition, compared with drying the absorbed support directly or using other conventional precipitating agents (such as sodium carbonate or sodium hydroxide), the present invention preferably uses carbon dioxide to in-situ precipitate the metal salt complex on the support, which is beneficial to increase the activity of the catalyst. Since carbon dioxide can easily enters the internal pores of the support, it is advantageous for sufficient precipitation of the metal salt complex solution such as metal ammonium salt, and facilitates uniform distribution of the precipitation; in addition, compared with conventional precipitants (such as sodium carbonate or sodium hydroxide), the present invention avoids the step of washing away the soluble salt adsorbed on the surface of the support after precipitation by a large amount of water, and the soluble salt produced in the present method can be removed merely by heating volatilization or decomposition.

(5) The catalyst of the present invention has low metal load, good dispersibility, high mechanical strength and lower cost, and has a good application prospect.

EMBODIMENTS

The invention is further described in detail below by way of specific examples, but it should not be understood that the scope of the invention is limited to the following examples. Various substitutions and modifications may be made without departing from the spirit and scope of the invention.

Gas chromatograph: Shimadzu GC-2014 (FID) detector, SE-30 capillary column (φ0.30 mm×30 m), injection port 270° C., detector 270° C.; temperature program: a constant temperature of 70° C. is kept for 1 min, then increased to 240° C. at a rate of 40° C./min, kept for 5 min.

Method for determination of hydroxyl value: see GB/T 12008.3-2009.

Method for determination of total amine value: the product is titrated with a 0.5 mol/L hydrochloric acid solution, and the total amine value of the product can be calculated by the mass of hydrochloric acid consumed.

Raw material conversion rate: total amine value of the product/total hydroxyl value of the raw material×100%.

Product yield: mass of polyether amine product/mass of polyether polyol raw material×100%.

The reductive amination reactor in the Examples is a fixed bed reactor.

Methylamine, dimethylamine, polyether polyols (PPG-230, T-2000, D-5000, T-403): Wanhua Chemical Group Co., Ltd.

The reagents used below are analytically pure if not explicitly stated.

In the following Examples, the support alumina used is WFC-05 type γ-alumina purchased from Zibo Wufeng Aluminum Magnesium Technology Co., Ltd.

EXAMPLE 1

Into 85 ml of formate solution containing 6.5 g of Ni, 7.5 g of Cu, 0.9 g of Pd and 0.2 g of Rh (based on the weight of the metal elements, the same as follows), ammonia water with a concentration of 25 wt % was added dropwise until the precipitate formed was completely dissolved, to obtain a mixed solution of metal ammonium salts. At room temperature, 84.9 g of dried strip-shaped alumina having a diameter of 3 mm was completely impregnated in the above solution, and the solution was allowed to stand for 5.5 hours and substantially completely adsorbed.

The impregnated support was taken out and placed in a tubular reactor, and was treated with carbon dioxide gas introduced at 45° C. for 4 hours, which was then slowly heated to 80° C. to dry for 12 hours.

Nitrogen gas was introduced to completely replace carbon dioxide in the tubular reactor, and part of the support was calcined at 450° C. for 4.5 h in nitrogen atmosphere. An excess barium hydroxide solution was used to absorb the $CO_2$ produced by the decomposition of the carbonate, so that the carbon dioxide was completely converted into barium carbonate precipitate, and 2 drops of phenolphthalein indicator was added into the solution which was then titrated with an oxalic acid standard solution having a concentration of c (mol/ml) until the color of the solution changed from red to colorless, while the volume a (ml) of the consumed oxalic acid standard solution was recorded. At the same time, the barium hydroxide solution without absorbing any $CO_2$ was used as a blank titration to record the volume b (ml) of the consumed oxalic acid standard solution. The mass of $CO_2$ produced after calcination of the catalyst can be calculated according to the following formula.

$$m = M*(b-a)*c$$

Wherein, m is the mass of carbon dioxide, g; M is the molecular weight of carbon dioxide, g/mol; a is the volume of the oxalic acid standard solution for sample titration, ml; b is the volume of the oxalic acid standard solution for blank titration, ml; c is the molar concentration of the oxalic acid standard solution, mol/ml.

After calculation, the carbon dioxide produced by the decomposition of carbonate is about 96% of the theoretical consumption of carbon dioxide, indicating that the metal salt has been sufficiently precipitated in the in-situ precipitation step of carbon dioxide.

The remaining support was reduced with a mixture of 5 vol % of hydrogen and 95 vol % of nitrogen at 200° C. for 12 h to obtain a supported catalyst A-1 containing 6.5 wt % of Ni, 7.5 wt % of Cu, 0.9 wt % of Pd and 0.2 wt % of Rh.

EXAMPLE 2

Into 86 ml of nitrate solution containing 10.0 g of Ni, 3.0 g of Cu, 0.5 g of Pd, 0.3 g of Rh and 0.1 g of Zr, ammonia water with a concentration of 25 wt % was added dropwise until the precipitate formed was completely dissolved to obtain a mixed solution of metal ammonium salts. At room temperature, 86.1 g of dried strip-shaped alumina having a diameter of 3 mm was completely impregnated in the above solution, and the solution was allowed to stand for 6 hours and substantially completely adsorbed.

The impregnated support was placed in a tubular reactor and heated to 35° C., and was treated with the introduced carbon dioxide for 6 h, which was then slowly heated to 80° C. to dry for 10 h, calcined at 400° C. for 4 h, cooled, and then reduced at 250° C. with a mixed gas of 50 vol % of hydrogen and 50 vol % of nitrogen for 8 hours to obtain a supported catalyst A-2 containing 10.0 wt % of Ni, 3.0 wt % of Cu, 0.5 wt % of Pd, 0.3 wt % of Rh and 0.1 wt % of Zr.

EXAMPLE 3

Into 86 ml of nitrate solution containing 8.5 g of Ni, 4.5 g of Cu, 0.65 g of Pd, 0.5 g of Rh and 0.45 g of Mg, ammonia water with a concentration of 28 wt % was added dropwise until the precipitate formed was completely dissolved to obtain a mixed solution of metal ammonium salts. At room temperature, 85.4 g of dried spherical alumina having a diameter of 3 mm was completely impregnated in the above solution, and the solution was allowed to stand for 8 hours and substantially completely adsorbed.

The impregnated support was placed in a tubular reactor and heated to 40° C., and was treated with the introduced carbon dioxide for 5 h, which was then slowly heated to 85° C. to dry for 8 h, calcined at 450° C. for 3 h, cooled, and then reduced at 100° C. with a mixed gas of 20 vol % of hydrogen and 80 vol % of nitrogen for 16 hours to obtain a supported catalyst A-3 containing 8.5 wt % of Ni, 4.5 wt % of Cu, 0.65 wt % of Pd, 0.5 wt % of Rh and 0.45 wt % of Mg.

EXAMPLE 4

Into 84 ml of acetate solution containing 9.5 g of Ni, 5.0 g of Cu, 0.7 g of Pd, 0.4 g of Rh, 0.25 g of Ce, 0.15 g of Mo, 0.05 g of Ti and 0.05 g of Fe, ammonia water with a concentration of 30 wt % was added dropwise until the precipitate formed was completely dissolved to obtain a mixed solution of metal ammonium salts. At room temperature, 83.9 g of dried clover-type alumina having a diameter of 3 mm was completely impregnated in the above solution, and the solution was allowed to stand for 5 hours, and the solution was substantially completely adsorbed.

The impregnated support was placed in a tubular reactor and heated to 30° C., and was treated with the introduced carbon dioxide for 4 h, which was then slowly heated to 90° C. to dry for 6 h, calcined at 300° C. for 8 h, cooled, and then reduced at 250° C. with a mixed gas of 5 vol % of hydrogen and 95 vol % of nitrogen for 24 hours to obtain a supported catalyst A-4 containing 9.5 wt % of Ni, 5.0 wt % of Cu, 0.7 wt % of Pd, 0.4 wt % of Rh, 0.24 wt % of Ce, 0.15 g of Mo, 0.05 g of Ti and 0.05 g of Fe.

EXAMPLE 5

Into 86 ml of nitrate solution containing 12.0 g of Ni, 1.0 g of Cu, 0.8 g of Pd, 0.2 g of Rh, 0.1 g of Ce, 0.27 g of Mg, 0.03 g of Zn, and 0.1 g of Sn, ammonia water with a concentration of 25 wt % was added dropwise until the precipitate formed was completely dissolved to obtain a mixed solution of metal ammonium salts. At room temperature, 85.5 g of dried strip-shaped alumina having a diameter of 2 mm was completely impregnated in the above solution, and the solution was allowed to stand for 7 hours and substantially completely adsorbed.

The impregnated support was placed in a tubular reactor and heated to 50° C., and was treated with the introduced carbon dioxide for 2 h, which was then slowly heated to 60° C. to dry for 12 h, calcined at 500° C. for 2 h, cooled, and then reduced at 300° C. with pure hydrogen for 4 hours to obtain a supported catalyst A-5 containing 12.0 wt % of Ni, 1.0 wt % of Cu, 0.8 wt % of Pd, 0.2 wt % of Rh, 0.1 wt % of Ce, 0.27 wt % of Mg, 0.03 wt % of Zn and 0.1 wt % of Sn.

EXAMPLE 6

Into 88 ml of oxalate solution containing 5.0 g of Ni, 5.5 g of Cu, 1.0 g of Pd, 0.3 g of Rh, 0.05 g of Zr, 0.3 g of Mg, 0.07 g of Zn, 0.05 g of Fe and 0.03 g of Sn, ammonia water with a concentration of 25 wt % was added dropwise until the precipitate formed was completely dissolved to obtain a mixed solution of metal ammonium salts. At room temperature, 87.7 g of dried cylindrical alumina having a diameter of 3 mm was completely impregnated in the above solution, and the solution was allowed to stand for 6 hours and substantially completely adsorbed.

The impregnated support was placed in a tubular reactor and heated to 20° C., and was treated with the introduced carbon dioxide for 10 h, which was then slowly heated to 85° C. to dry for 10 h, calcined at 400° C. for 4 h, cooled, and then reduced at 240° C. with pure hydrogen for 10 hours to obtain a supported catalyst A-6 containing 5.0 wt % of Ni, 5.5 wt % of Cu, 1.0 wt % of Pd, 0.3 wt % of Rh, 0.05 wt % of Zr, 0.3 wt % of Mg, 0.07 wt % of Zn, 0.05 wt % of Fe and 0.03 wt % of Sn.

EXAMPLE 7

Into 87 ml of nitrate solution containing 4.0 g of Ni, 8.0 g of Cu, 0.6 g of Pd, 0.05 g of Rh, 0.1 g of Mg, 0.15 g of Ce, 0.08 g of Mo and 0.12 g of Fe, ammonia water with a concentration of 28 wt % was added dropwise until the precipitate formed was completely dissolved to obtain a mixed solution of metal ammonium salts. At room temperature, 86.9 g of dried strip-shaped alumina having a diameter of 3 mm was completely impregnated in the above solution, and the solution was allowed to stand for 6 hours and substantially completely adsorbed.

The impregnated support was placed in a tubular reactor and heated to 35° C., and was treated with the introduced carbon dioxide for 7 h, slowly heated to 50° C. and dried for 24 h, calcined at 350° C. for 6 h, cooled, and then reduced at 220° C. with pure hydrogen for 10 hours to obtain a supported catalyst A-7 containing 7.5 wt % of Ni, 8.0 wt % of Cu, 0.6 wt % of Pd, 0.1 wt % of Rh, 0.1 wt % of Mg, 0.15 wt % of Ce, 0.08 wt % of Mo and 0.12 wt % of Fe.

EXAMPLE 8

Into 88 ml of nitrate solution containing 1.0 g of Ni, 10.0 g of Cu, 0.3 g of Pd, 0.15 g of Rh, 0.2 g of Zr, 0.04 g of Ce, 0.05 g of Mo, 0.1 g of Ti and 0.06 g of Sn, ammonia water with a concentration of 25 wt % was added dropwise until the precipitate formed was completely dissolved to obtain a mixed solution of metal ammonium salts. At room temperature, 88.1 g of dried spherical alumina having a diameter of 2 mm was completely impregnated in the above solution, and the solution was allowed to stand for 7 hours and substantially completely adsorbed.

The impregnated support was placed in a tubular reactor and heated to 35° C., and was treated with the introduced carbon dioxide for 6 h, which was then slowly heated to 120° C. to dry for 4 h, calcined at 600° C. for 5 h, cooled, and then reduced at 400° C. with pure hydrogen for 1 hours to obtain a supported catalyst A-8 containing 1.0 wt % of Ni, 10.0 wt % of Cu, 0.3 wt % of Pd, 0.15 wt % of Rh, 0.2 wt % of Zr, 0.04 wt % of Ce, 0.05 wt % of Mo, 0.1 wt % of Ti and 0.06 wt % of Sn.

EXAMPLE 9

Into 84 ml of nitrate solution containing 15.0 g of Ni, 0.5 g of Cu, 0.1 g of Pd, 0.25 g of Rh, 0.3 g of Zr and 0.05 g of Mg, ammonia water with a concentration of 28 wt % was added dropwise until the precipitate formed was completely dissolved to obtain a mixed solution of metal ammonium salts. At room temperature, 83.8 g of dried spherical alumina having a diameter of 3 mm was completely impregnated in the above solution, and the solution was allowed to stand for 6 hours and substantially completely adsorbed.

The impregnated support was placed in a tubular reactor and heated to 40° C., and was treated with the introduced carbon dioxide was introduced 8 h, which was then slowly heated to 85° C. to dry for 6 h, calcined at 200° C. for 12 h, cooled, and then reduced at 240° C. with a mixed gas of 10 vol % of hydrogen and 90 vol % of nitrogen for 12 hours to obtain a supported catalyst A-9 containing 15 wt % of Ni, 0.5 wt % of Cu, 0.1 wt % of Pd, 0.25 wt % of Rh, 0.3 wt % of Zr and 0.05 wt % of Mg.

EXAMPLE 10

Into 84 ml of nitrate solution containing 6.0 g of Ni, 9.5 g of Cu, 0.4 g of Pd, 0.35 g of Rh and 0.05 Mg, ammonia water with a concentration of 25 wt % was added dropwise until the precipitate formed was completely dissolved to obtain a mixed solution of metal ammonium salts. At room temperature, 83.7 g of dried strip-shaped alumina having a diameter of 3 mm was completely impregnated in the above solution, and the solution was allowed to stand for 7 hours and substantially completely adsorbed.

The impregnated support was placed in a tubular reactor and heated to 30° C., and was treated with the introduced carbon dioxide for 8 h, which was then slowly heated to 80° C. to dry for 6 h, calcined at 350° C. for 10 h, cooled, and then reduced at 200° C. with a mixed gas of 25 vol % of hydrogen and 75 vol % of nitrogen for 8 hours to obtain a supported catalyst A-10 containing 6 wt % of Ni, 9.5 wt % of Cu, 0.4 wt % of Pd, 0.35 wt % of Rh and 0.05 wt % of Mg.

EXAMPLE 11

Into 86 ml of nitrate solution containing 7.0 g of Ni, 6.5 g of Cu, 0.75 g of Pd, 0.15 g of Rh, 0.15 g of Zr and 0.15 Mg, ammonia water with a concentration of 25 wt % was added dropwise until the precipitate formed was completely dissolved to obtain a mixed solution of metal ammonium salts. At room temperature, 85.3 g of dried clover-type alumina having a diameter of 3 mm was completely impregnated in the above solution, and the solution was allowed to stand for 5 hours and substantially completely adsorbed.

The impregnated support was placed in a tubular reactor and heated to 35° C., and was treated with the introduced carbon dioxide for 7 h, slowly heated to 85° C. and dried for 6 h, calcined at 450° C. for 8 h, cooled, and then reduced at 300° C. with pure hydrogen for 4 hours to obtain a supported catalyst A-11 containing 7 wt % of Ni, 6.5 wt % of Cu, 0.75 wt % of Pd, 0.15 wt % of Rh, 0.15 wt % of Zr and 0.15 wt % of Mg.

EXAMPLE 12

Into 85 ml of nitrate solution containing 8.0 g of Ni, 7.0 g of Cu, 0.25 g of Pd, 0.05 g of Rh, and 0.2 g of Zr, ammonia water with a concentration of 25 wt % was added dropwise until the precipitate formed was completely dissolved to obtain a mixed solution of metal ammonium salts. At room temperature, 84.5 g of dried cylindrical alumina having a diameter of 3 mm was completely impregnated in the above solution, and the solution was allowed to stand for 6 hours and substantially completely adsorbed.

The impregnated support was placed in a tubular reactor and heated to 40° C., and was treated with the introduced carbon dioxide for 5 h, which was then slowly heated to 80° C. to dry for 12 h, calcined at 500° C. for 4 h, cooled, and then reduced at 350° C. with pure hydrogen for 5 hours to obtain a supported catalyst A-12 containing 8.0 wt % of Ni, 7.0 wt % of Cu, 0.25 wt % of Pd, 0.05 wt % of Rh and 0.2 wt % of Zr.

EXAMPLE 1-1

The difference from Example 1 is that the metal salt solution was not further prepared into a metal ammonium salt solution but was directly used for adsorption of the support; in addition, the adsorbed wet support is directly subjected to drying, calcination and reduction treatment. The supported catalyst A-1-1 was obtained.

COMPARATIVE EXAMPLE 1

The difference from Example 1 is that Rh is not contained in the mixed solution of the metal ammonium salts. The supported catalyst D-1 was obtained.

EXAMPLE 13

Amination of Diethylene Glycol (M=106)

A fixed-bed reactor was loaded with supported catalyst A-1 having a bulk volume of 30 ml. The reaction temperature was raised to 250° C. and the system pressure (absolute pressure, the same as follows) was raised to 10 MPa, then starting to feed the reactor. The space velocity of diethylene glycol was 0.3 h$^{-1}$, the molar ratio of liquid ammonia/diethylene glycol was 60:1, and the molar ratio of hydrogen/diethylene glycol was 1:1. The reactants were distilled to remove excess ammonia and water, and analyzed by gas chromatography. The content of diaminodiethylene glycol was 99.6 wt %, the content of morpholine was 0.4 wt %, and monoaminodiethylene glycol and diethylene glycol were not detected. According to the sampling and analysis after 120 h, the result was unchanged. The conversion rate of the raw material was 100%, and the yield of the amination product was 99.6%.

EXAMPLE 14

Amination of Dipropylene Glycol (M=134)

A fixed-bed reactor was loaded with supported catalyst A-2 having a bulk volume of 30 ml. The reaction temperature was lowered to 210° C. and the system pressure was raised to 18 MPa, then starting to feed the reactor. The space velocity of dipropylene glycol was 0.75 h$^{-1}$, the molar ratio of ammonia/dipropylene glycol was 30:1, and the molar ratio of hydrogen/dipropylene glycol was 0.05:1. The reactants were distilled to remove excess ammonia and water, and analyzed by gas chromatography. The content of diaminodipropylene glycol was 99.5 wt %, the content of dimethylmorpholine was 0.5 wt %, and monoaminodipropylene glycol and dipropylene glycol were not detected. According to the sampling and analysis after 150 h, the result was unchanged. The conversion rate of the raw material was 100%, and the yield of the amination product was 99.5%.

EXAMPLE 15

Amination of Polyether Polyol PPG-230 (Difunctional, Molecular Weight of 230)

A fixed-bed reactor was loaded with supported catalyst A-3 having a bulk volume of 30 ml. The reaction temperature was raised to 220° C. and the system pressure was raised to 15 MPa, then starting to feed the reactor. The space velocity of PPG-230 was 3 h$^{-1}$, the molar ratio of liquid ammonia/PPG-230 was 6:1, and the molar ratio of hydrogen/PPG-230 was 0.5:1. The reactants were distilled to remove excess ammonia and water, and analyzed by gas chromatography. The content of diamination product was 99.8 wt %, the monoamination product and PPG-230 were not detected, and the content of dimethylmorpholine was 0.2 wt %. According to sampling and analysis after 200 h, the result was unchanged. The conversion rate of the raw material was 100%, and the yield of the amination product was 99.8%.

EXAMPLE 16

Amination of Polyether Polyol T-2000 (Trifunctional, Molecular Weight of 2000)

A fixed-bed reactor was loaded with supported catalyst A-4 having a bulk volume of 30 ml. The reaction temperature was lowered to 180° C., and the system pressure was raised to 12 MPa, then starting to feed the reactor. The space velocity of T-2000 was 0.5 h$^{-1}$, the molar ratio of liquid ammonia/T-2000 was 20:1, and the molar ratio of hydrogen/T-2000 was 0.7:1. The reactants were distilled to remove excess ammonia and water, and analyzed by gas chromatography. The content of triamination product was 99.7 wt %, the diamination product, monoamination product and T-2000 were not detected, and the content of dimethylmorpholine was 0.3 wt %. According to the sampling and analysis after 200 h, the result was unchanged. The conversion rate of the raw material was 100%, and the yield of the amination product was 99.7%.

EXAMPLE 17

Amination of Polyether Polyol D-5000 (Difunctional, Molecular Weight of 5000)

A fixed-bed reactor was loaded with supported catalyst A-5 having a bulk volume of 30 ml. The reaction temperature was lowered to 150° C., and the system pressure was raised to 16 MPa, then starting to feed the reactor. The space velocity of D-5000 was 2.0 h$^{-1}$, the molar ratio of liquid ammonia/D-5000 was 13:1, and the molar ratio of hydrogen/D-5000 was 0.2:1. The reactants were distilled to remove excess ammonia and water, and analyzed by gas chromatography. The content of diamination product was 99.9 wt %, the monoamination product and D-5000 were not detected, and the content of dimethylmorpholine was 0.1 wt %. According to the sampling and analysis after 150 h, the result was unchanged. The conversion rate of the raw material was 100%, and the yield of the amination product was 99.9%.

EXAMPLE 18

Amination of Polyether Polyol T-403 (Trifunctional, Molecular Weight of 400)

A fixed-bed reactor was loaded with supported catalyst A-6 having a bulk volume of 30 ml. The reaction temperature was raised to 225° C., and the system pressure was raised to 20 MPa, then starting to feed the reactor. The space velocity of T-403 was 1.5 h$^{-1}$, the molar ratio of liquid ammonia/T-403 was 18:1, and the molar ratio of hydrogen/T-403 was 0.4:1. The reactants were distilled to remove excess ammonia and water, and analyzed by gas chromatography. The content of triamination product was 99.6 wt %, the diamination product, monoamination product and T-403 raw material were not detected, and the content of dimethylmorpholine was 0.4 wt %. According to the sampling and analysis after 150 h, the result was unchanged. The conversion rate of the raw material was 100%, and the yield of the amination product was 99.6%.

EXAMPLE 19

Methylation of Polyether Polyol D-400 (Difunctional, Molecular Weight of 400)

A fixed-bed reactor was loaded with supported catalyst A-7 having a bulk volume of 30 ml. The reaction temperature was lowered to 190° C., and the system pressure was raised to 15 MPa, then starting to feed the reactor. The space velocity of D-400 was 0.1 h$^{-1}$, the molar ratio of methylamine/D-400 was 10:1, and the molar ratio of hydrogen/D-400 was 0.35:1. The reactants were distilled to remove excess methylamine and water, and analyzed by gas chromatography. The content of di(methylamination) product was 99.8 wt %, the mono(methylamination) product and D-400 raw material were not detected, and the content of others were 0.2 wt % totally. According to the sampling and analysis after 150 h, the result was unchanged. The conversion rate of the raw material was 100%, and the yield of the amination product was 99.8%.

EXAMPLE 20

Dimethylation of Polyether Polyol D-2000 (Difunctional, Molecular Weight of 2000)

A fixed-bed reactor was loaded with supported catalyst A-8 having a bulk volume of 30 ml. The reaction temperature was lowered to 230° C., and the system pressure was raised to 5 MPa, then starting to feed the reactor. The space velocity of D-2000 was 0.5 h$^{-1}$, the molar ratio of dimethylamine/D-2000 was 15:1, and the molar ratio of hydrogen/D-2000 was 0.1:1. The reactants were distilled to remove excess dimethylamine and water, and analyzed by gas chromatography. The content of di(dimethylamination) product was 99.7 wt %, the mono(dimethylamination) product and D-2000 raw material were not detected, and the content of others were 0.3 wt % totally. According to the sampling and analysis after 150 h, the result was unchanged. The conversion rate of the raw material was 100%, and the yield of the amination product was 99.7%.

EXAMPLE 21

Amination of Polyether Polyol D-600 (Difunctional, Molecular Weight of 600)

A fixed-bed reactor was loaded with supported catalyst A-9 having a bulk volume of 30 ml. The reaction temperature was lowered to 165° C., and the system pressure was raised to 13 MPa, then starting to feed the reactor. The space velocity of D-600 was 0.6 If, the molar ratio of liquid ammonia/D-600 was 16:1, and the molar ratio of hydrogen/D-600 was 0.25:1. The reactants were distilled to remove excess ammonia and water, and analyzed by gas chromatography. The content of diamination product was 99.9 wt %, the monoamination product and D-600 were not detected, and the content of dimethylmorpholine was 0.1 wt %. According to the sampling and analysis after 160 h, the result was unchanged. The conversion rate of the raw material was 100%, and the yield of the amination product was 99.9%.

EXAMPLE 22

Methylation of Polyether Polyol D-600 (Difunctional, Molecular Weight of 600)

A fixed-bed reactor was loaded with supported catalyst A-10 having a bulk volume of 30 ml. The reaction temperature was raised to 215° C., the system pressure was raised to 17 MPa, then starting to feed the reactor. The space velocity of D-600 was 0.6 h$^{-1}$, the molar ratio of methylamine/D-600 was 19:1, and the molar ratio of hydrogen/D-600 was 0.15:1. The reactants were distilled to remove excess methylamine and water, and analyzed by gas chromatography. The content of di(methylamination) product was 99.8 wt %, the mono(methylamination) product and D-600 raw material were not detected, and the content of others were 0.2 wt % totally. According to the sampling and analysis after 180 h, the result was unchanged. The conversion rate of the raw material was 100%, and the yield of the amination product was 99.8%.

EXAMPLE 23

Dimethylation of Polyether Polyol D-600 (Difunctional, Molecular Weight of 600)

A fixed-bed reactor was loaded with supported catalyst A-11 having a bulk volume of 30 ml. The reaction temperature was lowered to 200° C., and the system pressure was raised to 18 MPa, then starting to feed the reactor. The space velocity of D-600 was 1.0 h$^{-1}$, the molar ratio of dimethylamine/D-600 was 12:1, and the molar ratio of hydrogen/D-600 was 0.3:1. The reactant was distilled to remove excess dimethylamine and water, and analyzed by gas chromatography. The content of di(dimethylamination) product was 99.6 wt %, the mono(dimethylamination) product and D-600 raw material were not detected, and the content of others were 0.4 wt % totally. According to the sampling and analysis after 120 h, the result was unchanged. The conversion rate of the raw material was 100%, and the yield of the amination product was 99.6%.

EXAMPLE 24

Amination of Polyether Polyol T-3000 (Trifunctional, Molecular Weight of 3000)

A fixed-bed reactor was loaded with supported catalyst A-12 having a bulk volume of 30 ml. The reaction temperature was lowered to 180° C., and the system pressure was raised to 16 MPa, then starting to feed the reactor. The space velocity of T-3000 was 0.5 h$^{-1}$, the molar ratio of liquid ammonia/T-3000 was 18:1, and the molar ratio of hydrogen/T-3000 was 0.35:1. The reactants were distilled to remove excess ammonia and water, and analyzed by gas chromatography. The content of diamination product was 99.7 wt %, the monoamination product and T-3000 raw material were not detected, and the content of dimethylmorpholine was 0.3 wt %. According to the sampling and analysis after 210 h, the result was unchanged. The conversion rate of the raw material was 100%, and the yield of the amination product was 99.7%.

EXAMPLE 25

The difference from Example 13 was that the reaction was carried out using Catalyst A-1-1.

Upon detection, the reaction results were as follows: the content of diaminodiglycol was 92.6 wt %, the content of morpholine was 2.1 wt %, the content of monoaminodiglycol was 5.3 wt %, and diglycol were not detected. According to the sampling and analysis after 120 h, the result was unchanged. The conversion rate of the raw material was 100%, and the yield of amination product was 90.6%.

COMPARATIVE EXAMPLE 2

The difference from Example 13 was that the reaction was carried out using Catalyst D-1.

Upon detection, the reaction results were as follows: the content of diaminodiglycol was 93.6 wt %, the content of morpholine was 1.4 wt %, the content of monoaminodiglycol was 5.0 wt %, and diglycol was not detected. According to the sampling and analysis after 120 h, the result was unchanged. The conversion rate of the raw material was 100%, and the yield of the amination product was 90.6%.

COMPARATIVE EXAMPLE 3

The catalyst was prepared according to the method described in Example 1 of CN102336903A by reacting a NaOH solution with a Ni—Al alloy. By adjusting the amount of NaOH added, the prepared catalyst had a Ni content of 90 wt % and an Al content of 10 wt %. The catalyst was evaluated according to the amination of polyether polyol PPG-230 (difunctional, molecular weight of 230) in Example 15 of the present application. Using gas chromatography to analyze the reaction products: the content of diamination product was 90.5 wt %, the content of monoamination product was 2.0 wt %, the content of dimethylmorpholine was 2.5 wt %, and the content of raw material was 5.0 wt %. According to the sampling and analysis after 50 h, the result was unchanged. The conversion rate of the raw material was 95%, and the yield of the amination product was 92.5%.

COMPARATIVE EXAMPLE 4

The catalyst was prepared according to the method described in Example 1 of CN102336903A by reacting a NaOH solution with a Ni—Al alloy. By adjusting the amount of NaOH added, the prepared catalyst had a Ni content of 95 wt % and an Al content of 5 wt %. The catalyst was evaluated according to the amination of polyether polyol T-403 (trifunctional, molecular weight of 400) in Example 18 of the present application. Using gas chromatography to analyze the reaction products: the content of triamination product was 85.6 wt %, the content of diamination product was 3.4 wt %, the content of monoamination product was 2.0 wt %, the content of dimethylmorpholine content was 1.0 wt %, and the content of raw material T-403 was 8.0 wt %. According to the sampling and analysis after 100 h, the result was unchanged. The conversion rate of the raw material was 92%, and the yield of the amination product was 91.0%.

Conclusion: It can be seen from the above description that the specific combination of the active components of nickel, copper, palladium and rhodium in the catalyst of the present invention can greatly reduce by-products in the amination process of polyether polyol (eg, monoamino and/or bisamino by-products, dimethylmorpholine by-products generated by low molecular weight polyethers, etc.), especially under the conditions that the polyether polyol is completely converted, thereby greatly improving the selectivity and product yield of primary amines.

The invention claimed is:

1. A supported catalyst used for synthesizing polyether amines, comprising a support and active components, wherein the active components comprises: 1-15 wt % of Ni, 0.5-10 wt % of Cu, 0.1-1.0 wt % of Pd, and 0.05-0.5 wt % of Rh, based on the total weight of the catalyst.

2. The supported catalyst according to claim 1, wherein the active components of the catalyst comprises: 4-12 wt % of Ni, 1-8 wt % of Cu, 0.5-0.8 wt % of Pd, and 0.15-0.4 wt % Rh, based on the total weight of the catalyst.

3. The supported catalyst according to claim 2, wherein the active components of the catalyst comprises: 5-10 wt % of Ni, 3-5 wt % of Cu, 0.6-0.7 wt % of Pd, and 0.2-0.3 wt % of Rh, based on the total weight of the catalyst.

4. The supported catalyst according to claim 2, wherein the catalyst optionally comprises an auxiliary agent which is selected from the group consisting of Zr, Cr, Mo, Fe, Zn, Sn, Bi, Ce, La, Hf, Sr, Sb, Mg, Be, Re, Ta, Ti, Sc, Ge, and any combination thereof, preferably the group consisting of Zr, Ce, Mg, Mo, Ti, and any combination thereof, more preferably Zr and/or Mg.

5. The supported catalyst according to claim 1, wherein the catalyst optionally comprises an auxiliary agent which is selected from the group consisting of Zr, Cr, Mo, Fe, Zn, Sn, Bi, Ce, La, Hf, Sr, Sb, Mg, Be, Re, Ta, Ti, Sc, Ge, and any combination thereof, preferably the group consisting of Zr, Ce, Mg, Mo, Ti, and any combination thereof, more preferably Zr and/or Mg.

6. The supported catalyst according to claim 5, wherein the content of the auxiliary agent is 0-0.5 wt %, preferably 0.05-0.45 wt %, more preferably 0.1-0.3 wt %, based on the total weight of the catalyst.

7. The supported catalyst according to claim 5, wherein the total content of the active components is not less than 5 wt %, preferably not less than 10 wt %, based on the total weight of the catalyst.

8. The supported catalyst according to claim 5, wherein the support is selected from the group consisting of porous γ-Al$_2$O$_3$, SiO$_2$, MgO, TiO$_2$, ZrO$_2$, and any combination thereof, preferably γ-Al$_2$O$_3$.

9. The supported catalyst according to claim 1, wherein the total content of the active components is not less than 5 wt %, preferably not less than 10 wt %, based on the total weight of the catalyst.

10. The supported catalyst according to claim 1, wherein the support is selected from the group consisting of porous γ-Al$_2$O$_3$, SiO$_2$, MgO, TiO$_2$, ZrO$_2$, and any combination thereof, preferably γ-Al$_2$O$_3$.

11. A method of preparing the supported catalyst according to claim 1, wherein the method comprises the following steps:
1) Preparation of a metal salt solution: weighing metal salts proportionally, and adding deionized water to prepare a metal salt solution; wherein the metal salts are metal salts of the active components and the optional auxiliary agent;
2) Adsorption: adding the support to adsorb the metal salt complex solution obtained in step 1) to obtain an adsorbed wet support;
3) Drying, calcining, and reducing the wet support to obtain the supported catalyst.

12. The method according to claim 11, wherein the metal salt is one or more of metal halide, metal nitrate, organic acid metal salt, preferably one or more of metal nitrate, metal formate, metal acetate and metal oxalate, more preferably metal nitrate.

13. The method according to claim 12, wherein the method further comprises step 1a) preparation of a metal salt complex solution: forming a metal salt complex solution by reacting the metal salt solution with a ligand; preferably, the ligand is one or more of ammonia and organic amines, more preferably one or more of ammonia, EDTA and diethylamine.

14. The method according to claim 11, wherein the method further comprises step 1a) preparation of a metal salt complex solution: forming a metal salt complex solution by reacting the metal salt solution with a ligand; preferably, the ligand is one or more of ammonia and organic amines, more preferably one or more of ammonia, EDTA and diethylamine.

15. The method according to claim 14, wherein the method further comprises step 2a) in-situ precipitation of $CO_2$: precipitating the metal salt complex on the adsorbed wet support obtained in the step 2) by using carbon dioxide gas;
preferably, the reaction condition for in-situ precipitation of $CO_2$ is: performing the precipitation reaction in an atmosphere containing carbon dioxide at a reaction temperature of 20° C.-50° C., preferably 30° C.-40° C. for 2 h-10 h, preferably 4 h-6 h.

16. A method for preparing a polyether amine by amination of a polyether polyol, wherein the method is as follow: subjecting the polyether polyol to a reductive amination reaction in the presence of hydrogen, an amination reagent and a supported catalyst to prepare a polyether amine; wherein the supported catalyst is prepared by the method according to claim 11.

17. A method for preparing a polyether amine by amination of a polyether polyol, wherein the method is as follow: subjecting the polyether polyol to a reductive amination reaction in the presence of hydrogen, an amination reagent and a supported catalyst to prepare a polyether amine; wherein the supported catalyst is the supported catalyst according to claim 1.

18. The method according to claim 17, wherein the polyether polyol contains an EO and/or PO skeleton and has a weight average molecular weight of 90-7,000, preferably a molecular weight of 100-5,000, more preferably a molecular weight of 200-600.

19. The method for preparing a polyether amine by amination of a polyether polyol according to claim 18, wherein the space velocity of the polyether polyol is 0.01-3 $h^{-1}$, preferably 0.1-1.0 $h^{-1}$.

20. The method according to claim 17, wherein the space velocity of the polyether polyol is 0.01-3 $h^{-1}$, preferably 0.1-1.0 $h^{-1}$.

* * * * *